United States Patent
Chandar et al.

(10) Patent No.: US 8,206,754 B2
(45) Date of Patent: Jun. 26, 2012

(54) PERSONAL CARE COMPOSITION WITH COCOA BUTTER AND DIHYDROXYPROPYL AMMONIUM SALTS

(75) Inventors: Prem Chandar, Closter, NJ (US); Wei Dong Tian, Shelton, CT (US); Daniel Alfred Tempesta, Waterbury, CT (US); Zhi-xing Jiang, Southbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 659 days.

(21) Appl. No.: 11/755,008

(22) Filed: May 30, 2007

(65) Prior Publication Data

US 2008/0299237 A1    Dec. 4, 2008

(51) Int. Cl.
*A61K 36/00*    (2006.01)

(52) U.S. Cl. ....................................... 424/725

(58) Field of Classification Search .................. None
See application file for complete search history.

(56) References Cited

U.S. PATENT DOCUMENTS

| 7,175,836 | B1 | 2/2007 | Hart et al. | |
| 7,176,172 | B2 | 2/2007 | Harding et al. | |
| 2004/0018244 | A1* | 1/2004 | Piterski | 424/535 |
| 2006/0088495 | A1 | 4/2006 | Harichian et al. | |
| 2006/0088496 | A1 | 4/2006 | McManus et al. | |
| 2006/0089290 | A1 | 4/2006 | Mc Manus et al. | |
| 2007/0053853 | A1 | 3/2007 | Hurley et al. | |
| 2007/0054820 | A1 | 3/2007 | Harichian et al. | |

FOREIGN PATENT DOCUMENTS

| DE | 195 17 048 | | 5/1995 |
| DE | 102005003708 A1 | | 8/2006 |
| GB | 2 361 641 A | | 4/2000 |
| WO | 90/03161 | | 4/1990 |
| WO | 96/35410 | | 11/1996 |
| WO | WO 2006/045584 | * | 4/2006 |
| WO | 2006/045583 A1 | | 5/2006 |
| WO | 2006/045584 A1 | | 5/2006 |

OTHER PUBLICATIONS

Co-pending Appln.—Harichian et al.; U.S. Appl. No. 11/557,530, filed Nov. 8, 2006; For: Personal Care Compositions Containing Quaternary Ammonium Trihydroxy Substituted Dipropyl Ether.
Co-pending Appln.—Chandar et al.; filed: May 30, 2007; For: Personal Care Compositions With Enhanced Fragrance Delivery.
Co-pending Appln.—Yang et al.; filed: May 30, 2007; For: Enhanced Delivery of Certain Fragrance Components From Personal Care Compositions.
PCT International Search Report.
PCT Written Opinion.

* cited by examiner

*Primary Examiner* — Melenie McCormick
(74) *Attorney, Agent, or Firm* — Milton L. Honig

(57) ABSTRACT

A personal care composition is provided that when the composition is applied to the skin provides improved translucency to reveal a healthy skin color. The composition is based upon a mixture of dihydroxypropyl quaternary ammonium salt and cocoa butter.

2 Claims, No Drawings

PERSONAL CARE COMPOSITION WITH COCOA BUTTER AND DIHYDROXYPROPYL AMMONIUM SALTS

BACKGROUND OF THE INVENTION

1. Field of the Invention

The invention concerns personal care formulas, particularly for facial and body products, which allow visualization of underlying skin to be seen as having a healthy natural color.

2. The Related Art

Vitality is often evidenced by a person's face. Appealing features include a natural look of a person's own skin. Translucency is the property of a cosmetic formula which allows light to transfer into the epidermis so that underlying skin can be seen. This includes visualization of blood vessels. A pinkish healthy skin color emanates therefrom.

U.S. Pat. No. 7,175,836 B1 (Hart et al.) discloses a water-in-oil cosmetic composition containing conjugated linoleic acid which was shown to have an effect on improving brightness and radiance.

An object of the present invention is to provide a cosmetic composition which delivers a natural look of healthy color, particularly through achievement of improved translucency.

SUMMARY OF THE INVENTION

A personal care composition is provided which includes:
(i) from about 0.05% to about 30% by weight of a dihydroxypropyl quaternary ammonium salt of structure AB, wherein
  A is a cationic charged component of the salt AB,
  B is an anionic charged component of the salt AB, and
  A has a single quaternized nitrogen atom, at least two hydroxy groups and a molecular weight no higher than about 250;
(ii) from about 0.01 to about 30% by weight of cocoa butter.

DETAILED DESCRIPTION OF THE INVENTION

Now it has been found that translucency can be imparted to skin through a composition that includes dihydroxypropyl quaternary ammonium salts and cocoa butter.

Thus, an important material of the present invention is dihydroxypropyl quaternary ammonium salts of structure AB, wherein A is a cationic charged component of the salt AB, and B is an anionic charged component of the salt AB, A has one quaternized nitrogen atom, at least two hydroxyl groups and a molecular weight no higher than about 250 but preferably no higher than about 200, and optimally no higher than 170.

Anionic charged component B may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate. The number and charge of negatively charged component B will be sufficient to neutralize the positive charge of component A.

A preferred embodiment of the quaternary ammonium salts is the dihydroxypropyl tri($C_1$-$C_3$ alkyl or hydroxyalkyl) ammonium salts.

These salts may be obtained in a variety of synthetic procedures, most particularly by hydrolysis of chlorohydroxypropyltri($C_1$-$C_3$ alkyl or hydroxyalkyl)ammonium salts. Ordinarily the $C_1$-$C_3$ alkyl or hydroxyalkyl constituent on the quaternized ammonium group will be methyl, ethyl, n-propyl, isopropyl, hydroxyethyl, hydroxymethyl and mixtures thereof. Particularly preferred is a trimethyl ammonium group known through INCI nomenclature as a "trimonium" group. A most preferred species is 1,2-dihydroxypropyltrimonium chloride, wherein the $C_1$-$C_3$ alkyl is a methyl group.

Another useful species of the quaternary ammonium salts is the material of structure (I).

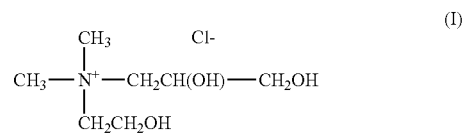

Amounts of the quaternary ammonium salts may range from about 0.05 to about 30%, preferably from about 0.1 to about 25%, more preferably from about 1 to about 15%, optimally from about 5 to about 10% by weight of the composition.

Another important component of the present invention is that of cocoa butter. The term "cocoa butter" is also defined as oleum theobromatis (theobroma oil). This material is obtained from the cacao bean by expression, decoction or extraction by solvent. Particularly common is a production method wherein cacao seeds are compressed between hot or cold plates. Typical properties are a specific gravity ranging from about 0.858 to 0.864 (100/25° C.), melting point between about 30 to about 35° C., refractive index (n 40/D) of about 1.4537 to 1.4585; saponification number about 188 to 200 and an iodine number from about 32 to 43. Amounts of the cocoa buffer may range from about 0.01 to about 30%, preferably from about 0.1 to about 15%, more preferably from about 0.5 to about 10%, and optimally from about 1% to about 5% by weight.

Emollient materials may serve as cosmetically acceptable carriers. These may be in the form of natural or synthetic esters, hydrocarbons and silicones. Amounts of the emollients may range anywhere from about 0.1 to about 60%, preferably between about 1 and about 30% by weight of the composition.

Among the ester emollients are:

(a) Alkyl esters of saturated fatty acids having 10 to 24 carbon atoms. Examples thereof include behenyl neopentanoate, isononyl isonanonoate, isopropyl myristate and octyl stearate.

(b) Ether-esters such as fatty acid esters of ethoxylated saturated fatty alcohols.

(c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

(d) Wax esters such as beeswax, spermaceti wax and tribehenin wax.

(e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$-$C_{13}$ isoparaffins, polybutenes, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

A wide variety of silicones including materials of liquid, solid or semi-solid consistency at room temperature can be useful as emollients for this invention. Liquid silicones include silicone oils which may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms. Commercially available volatile silicone oils include DC 200, DC 244, DC 245, DC 344 and DC 345, all supplied by the Dow Corning Corporation; SF-1204, SF-1202 Silicone Fluids, GE 7207 and GE 7158 sourced from GE Silicones; and SWS-03314 sourced from SWS Silicones Corporation.

Useful nonvolatile silicone oils include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5\times10^{-6}$ to 0.1 m$^2$/s at 25° C. Among the preferred nonvolatile emollients useful in the present compositions are the polydimethyl siloxanes having viscosities from about $1\times10^{-5}$ to about $4\times10^{-4}$ m$^2$/s at 25° C. Representative commercial materials include polyalkyl siloxanes sold under the Viscasil Series from G.E. Silicones, and the DC 200 series sold by the Dow Corning Corporation. Polyalkylaryl siloxanes including polymethylphenyl siloxanes such as SF 1075 methyl-phenyl fluid and 556 Cosmetic Grade Fluid (sold by Dow Corning Corporation) may also be useful. Illustrative polyoxyalkylene ether copolymers are commercially available as SF 1066 from G.E. Silicones, and PEG-10 Dimethicone available from Shin-Etsu.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Amounts of the silicone may range from about 0.05 to about 50%, preferably from about 0.5 to about 40%, more preferably from about 2 to about 20%, optimally from about 5 to about 12% by weight of the composition.

Surfactants may also be present in compositions of this invention. Total concentration of the surfactant when present may range from about 0.1 to about 50%, preferably from about 1 to about 25%, optimally from about 1 to about 10% by weight of the composition, and being highly dependent upon the type of personal care product. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Useful amphoteric surfactants include cocoamidopropyl betaine, $C_{12}$-$C_{20}$ trialkyl betaines, sodium lauroamphoacetate, and sodium laurodiamphoacetate.

Adjunct humectants may be employed in the present invention. These are generally polyhydric alcohol-type materials. Typical polyhydric alcohols include glycerin, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of adjunct humectant may range anywhere from about 0.2 to about 40%, preferably between 1 and 25%, most preferably between 2 and 15% by weight of the composition. Most preferred is glycerin as an adjunct humectant or moisturizer.

Sunscreen agents may also be included in compositions of the present invention. Particularly preferred are such materials as ethylhexyl p-methoxycinnamate, available as Parsol MCX®, Avobenzene available as Parsol 1789®, and benzophenone-3 also known as Oxybenzone. Inorganic sunscreen actives may be employed such as microfine (1 to 100 nm) titanium dioxide and zinc oxide. Amounts of the sunscreen agents when present may generally range from 0.1 to 30%, preferably from 2 to 20%, optimally from 4 to 10% by weight of the composition.

Preservatives can desirably be incorporated into the personal care compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.0001% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the composition.

Another type of useful substance can be that of an enzyme such as amylases, oxidases, proteases, lipases, cellulases, elastases and combinations.

Skin lightening compounds may be included in the compositions of the invention. Illustrative substances are placental extract, lactic acid, niacinamide, arbutin, kojic acid, ferulic acid, *Pisum Sativum* (Actiwhite LS 9808, ex Cognis), resorcinol and derivatives including 4-substituted resorcinols and combinations thereof. Amounts of these agents may range from about 0.1 to about 10%, preferably from about 0.5 to about 2% by weight of the composition.

Sunless tanners may also be formulated with compositions of this invention. Representative of this category is dihydroxyacetone, erythrulose, Troxerutin, melanin, mahkanni and mixtures thereof. Adjunct agents include amino acids, peptides, amines and combinations. Amounts of the sunless tanner may range from about 0.1 to about 15%, preferably from about 0.5 to about 10%, optimally from about 1 to about 5% by weight.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, licorice, aloe vera, grape seed, citrus unshui, willow bark, sage, thyme and rosemary.

Also included may be such materials as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

Personal care compositions of the present invention may be in any form. These forms may include lotions, creams, roll-on formulations, sticks, mousses, aerosol and non-aerosol sprays and fabric (e.g. nonwoven textile)-applied formulations.

A wide variety of packaging can be employed to store and deliver the personal care compositions. Packaging is often dependent upon the type of personal care end-use. For instance, leave-on skin lotions and creams, sunless tanners and shower gels generally employ plastic containers with an opening at a dispensing end covered by a closure. Typical closures are screw-caps, non-aerosol pumps and flip-top hinged lids. Metallic cans pressurized by a propellant and having a spray nozzle serve as packaging for sprayable forms of the personal care products. Toilet bars may have packaging constituted by a cellulosic or plastic wrapper or within a cardboard box or even encompassed by a shrink wrap plastic film.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

It should be noted that in specifying any range of concentration or amount, any particular upper concentration can be associated with any particular lower concentration or amount.

The following examples will more fully illustrate the embodiments of this invention. All parts, percentages and proportions referred to herein and in the appended claims are by weight unless otherwise illustrated.

Example 1

A representative personal care composition of the present invention in the form of a cosmetic lotion is outlined under Table I.

TABLE I

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| Cocoa Butter | 3.00 |
| Dihydroxypropyltrimonium Chloride | 5.00 |
| PHASE B | |
| Xanthan Gum | 0.20 |
| Natrosol ® 250HHR (ethyl cellulose) | 0.50 |
| Butylene Glycol | 3.00 |
| Glycerin | 10.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12-15 Alkyl Octanoate | 3.00 |
| PHASE D | |
| Vitamin A Palmitate | 0.10 |
| Bisabolol | 0.01 |

TABLE I-continued

| INGREDIENT | WEIGHT % |
| --- | --- |
| Vitamin A Acetate | 0.01 |
| Fragrance | 0.03 |
| Retinol 50C | 0.02 |
| Conjugated Linoleic Acid | 0.50 |

Example 2

Illustrated herein is a skin cream incorporating a quat salt and cocoa butter of the present invention.

TABLE II

| INGREDIENT | WEIGHT % |
| --- | --- |
| Glycerin | 10.00 |
| Niacinamide | 5.00 |
| Dihydroxypropyltrimonium Chloride | 5.00 |
| Cocoa Butter | 5.00 |
| Permethyl 101A[1] | 3.00 |
| Sepigel 305[2] | 2.50 |
| Q2-1403[3] | 2.00 |
| Linseed Oil | 1.33 |
| Arlatone 2121[4] | 1.00 |
| Cetyl Alcohol CO-1695 | 0.72 |
| SEFA Cottonate[5] | 0.67 |
| Tocopherol Acetate | 0.50 |
| Panthenol | 0.50 |
| Stearyl Alcohol | 0.48 |
| Titanium Dioxide | 0.40 |
| Disodium EDTA | 0.10 |
| Glydant Plus[6] | 0.10 |
| PEG-100 Stearate | 0.10 |
| Stearic Acid | 0.10 |
| Purified Water | Balance |

[1]Isohexadecane, Presperse Inc., South Plainfield, NJ
[2]Polyacrylamide(and)C13-14 Isoparaffin(and) Laureth-7, Seppic Corporation, Fairfield, NJ
[3]dimethicone(and)dimethiconol, Dow Corning Corp. Midland, MI
[4]Sorbitan Monostearate and Sucrococoate, ICI Americas Inc., Wilmington, DE
[5]Sucrose ester of fatty acid
[6]DMDM Hydantoin (and) Iodopropynyl Butylcarbamate, Lonza Inc., Fairlawn, NJ

Example 3

Illustrative of another cosmetic composition incorporating the quat salt and cocoa butter according to the present invention is the formula of Table III.

TABLE III

| INGREDIENT | WEIGHT % |
| --- | --- |
| Polysilicone-11 | 29 |
| Cyclomethicone | 59 |
| Glycerin | 10 |
| Dihydroxypropyltrimonium Chloride | 1.2 |
| Dimethicone Copolyol | 0.5 |
| Cocoa Butter | 0.3 |

Example 4

A relatively anhydrous composition incorporating the quat salt and cocoa butter of the present invention is reported in Table IV.

TABLE IV

| INGREDIENT | WEIGHT % |
| --- | --- |
| Cyclomethicone | 60.65 |
| Glycerin | 11.00 |
| Dimethicone | 10.10 |
| Squalane | 6.00 |
| Cocoa Butter | 4.00 |
| Dihydroxypropyltrimonium Chloride | 5.00 |
| Isostearic Acid | 1.90 |
| Borage Seed Oil | 0.90 |
| Retinyl Palmitate | 0.25 |
| Ceramide 6 | 0.10 |
| Tocopherol | 0.10 |

Example 5

An aerosol packaged foaming cleanser with a quat salt and cocoa butter suitable for the present invention is outlined in Table V.

TABLE V

| INGREDIENT | WEIGHT % |
| --- | --- |
| Sunflower Seed Oil | 10.00 |
| Glycerin | 10.00 |
| Maleated Soybean Oil | 5.00 |
| Cocoa Butter | 1.00 |
| Polyglycero-4 Oleate | 1.00 |
| Sodium C14-16 Olefin Sulfonate | 15.00 |
| Sodium Lauryl Ether Sulphate (25% active) | 15.00 |
| Cocoamidopropylbetaine | 15.00 |
| DC 1784 ® (Silicone Emulsion 50%) | 5.00 |
| Polyquaternium-11 | 1.00 |
| Dihydroxypropyltrimonium Chloride | 1.00 |
| Water | Balance |

Example 6

A disposable, single use personal care towelette product is described according to the present invention. A 70/30 polyester/rayon non-woven towelette is prepared with a weight of 1.8 grams and dimensions of 15 cm by 20 cm. Onto this towelette is impregnated 1.0 grams of a composition including a quaternary ammonium salt and a silicone microemulsion as outlined in Table VI below.

TABLE VI

| INGREDIENT | WEIGHT % |
| --- | --- |
| Dihydroxypropyltrimonium Chloride | 4.00 |
| Glycerin | 12.00 |
| Cocoa Butter | 1.00 |
| Disodium Capryl Amphodiacetate | 1.00 |
| Gluconolactone | 0.90 |
| Silicone Microemulsion | 0.85 |
| Witch Hazel | 0.50 |
| PEG-40 Hydrogenated Castor Oil | 0.50 |
| Fragrance | 0.20 |
| Vitamin E Acetate | 0.001 |
| Water | Balance |

Example 7

A toilet bar illustrative of the present invention is outlined under Table VII.

TABLE VII

| INGREDIENT | WEIGHT % |
| --- | --- |
| Sodium Soap (85/15 Tallow/Coconut) | 77.77 |
| Dihydroxypropyltrimonium Chloride | 3.50 |
| Cocoa Butter | 2.00 |
| Sodium Chloride | 0.77 |
| Titanium Dioxide | 0.40 |
| Fragrance | 1.50 |
| Disodium EDTA | 0.02 |
| Sodium Etidronate | 0.02 |
| Fluorescer | 0.024 |
| Water | Balance |

Example 8

Herein is reported a body lotion incorporating the quat salt and cocoa butter of the present invention.

TABLE VIII

| INGREDIENT | WEIGHT % |
| --- | --- |
| Stearic Acid | 2.00 |
| Glycol Stearate/Stearamide AMP | 1.10 |
| Glycerol Monostearate | 0.55 |
| PEG-100 Stearate | 1.00 |
| Dimethicone | 1.00 |
| Isopropyl Palmitate | 2.50 |
| Cetyl Alcohol | 0.30 |
| Cocoa Butter | 1.00 |
| Dihydroxypropyltrimonium Chloride | 2.00 |
| Hydroxyethyl Acrylate/Sodium Acryloyldimethyl Taurate | 2.00 |
| Tetrasodium EDTA | 0.10 |
| Glycerin | 10.00 |
| DC 1501 (Cyclopentasiloxane and Dimethiconol) | 0.50 |
| Glydant Plus ® Liquid | 0.20 |
| Dihydroxyacetone | 1.50 |
| Erythrulose | 0.20 |
| Fragrance | 0.80 |
| Water | Balance |

Example 9

Translucency measurements are reported herein. Skin is a translucent substance. When light is incident on skin, a small portion is reflected and scattered at the skin surface. Most of the light continues to penetrate into the skin to be scattered that changes the propagation direction. A portion of light also gets absorbed by skin chromophores such as blood and melanin at deeper layers of skin. The scattering of light inside the skin changes the light path and results in light diffusion from its original path. After multiple scattering, some of the light survives absorption and manages to return to the skin surface to escape into the reflection space. This portion is referred to as the diffuse reflected light. This diffuse reflected light goes through the absorption by the blood and melanin and therefore carries the distinctive signature of the absorbents that give skin its unique color.

Total skin spectral reflectance is the sum of the reflectance at and beneath the skin surface. Translucency is the light penetration and diffusion inside the skin. It is dependent on the optical scattering and absorption properties of the skin. Translucency is low when the scattering and absorption coefficients are high. This corresponds to the appearance of skin being hard and opaque with more uneven texture. Translucency is high when the scattering and absorption coefficients are low. This corresponds to the appearance of skin being soft with more even texture.

Translucency is related to the spectral reflectance. Skin translucency increases as the surface scattering decreases and more light penetrates into the skin. Therefore, the increase of skin translucency corresponds to the decrease of the total spectral reflectance.

Measurements were performed with a Minolta Spectrophotometer CM-2500C. This instrument utilizes two pulsed xenon lamps as light source and operates over a wavelength range from 360 to 740 nm. The color space is defined by the well known $L^*a^*b^*$. Measurements were done by touching the spectrophotometer probe gently against the test area and taking three repeat reflectance spectra. These measurements were done at 10 minutes, 1 hour and 3 hours after product application.

Analysis of the data was as follows:
1. Reflectance spectra Change="Spectra after application"–"Spectra of baseline (before application)".
2. Delta $L^*=L^*$ after application–$L^*$ of baseline.
3. The translucency change was measured by delta $L^*$: decrease $L^*$ indicates more translucency.
4. The relative translucency was measured by normalized delta $L^*$.

The application areas were three body sites on the forearm ($4\times5$ cm$^2$). Samples and dosing were as follows.

Site 1: Apply 2 mg/cm$^2$ sample A
Site 2: Apply 0.5 mg/cm$^2$ sample B
Site 3: Apply 2 mg/cm$^2$ sample A with 0.5 mg/cm$^2$ sample B Sample A was a 12% dihydroxypropyltrimonium chloride in water. Sample B was 50% cocoa butter in a carrier oil (caprylic capric triglycerides).

Efficacy tests are reported in Table IX. The normalized translucency values represent the change of reflectance between baseline and sample applied reflectance spectra.

TABLE IX

| Sample | Active Ingredient | Normalized Translucency |
| --- | --- | --- |
| A (2 mg/cm$^2$) | Dihydroxypropyltrimonium Chloride | 0.8 |
| B (0.5 mg/cm$^2$) | Cocoa Butter | 0.2 |
| A + B (0.5 mg/cm$^2$) | Dihydroxypropyltrimonium Chloride and Cocoa Butter Mixture | 1.42 |

By itself, the cocoa butter (Sample B) had only a minor positive effect upon translucency. Sample A was the dihydroxypropyltrimonium chloride active which provided a much stronger improvement in translucency. Combination of the dihydroxypropyltrimonium chloride with cocoa butter unexpectedly gave a value of 1.42 revealing a substantial improvement in the healthy skin color property.

What is claimed is:
1. A personal care product comprising:
 (i) from 1% to 5% by weight of a dihydroxypropyl quaternary ammonium salt of structure AB,
  wherein A is a cationic charged component of the salt AB,
  B is an anionic charged component of the salt AB, and
  A has a single quaternized nitrogen atom, at least two hydroxy groups and a molecular weight no higher than about 250, and wherein the salt is dihydroxypropyltrimonium chloride;

(ii) from 0.5 to 1% by weight of cocoa butter; and wherein the dihydroxypropyltrimonium chloride and cocoa butter in combination improve translucency to reveal a healthy skin color.

2. A method for improving translucency to reveal a healthy skin color comprising applying to skin a personal care product according to claim 1.

\* \* \* \* \*